United States Patent
Nayar

(10) Patent No.: US 9,707,174 B2
(45) Date of Patent: Jul. 18, 2017

(54) AQUEOUS OPHTHALMIC SOLUTION OF OLOPATADINE

(71) Applicant: Gavis Pharmaceuticals, Somerset, NJ (US)

(72) Inventor: Bala Chandran Nayar, Somerset, NJ (US)

(73) Assignee: Somerset Therapeutics LLC, Mendham, NJ (US)

( * ) Notice: Subject to any disclaimer, the term of this patent is extended or adjusted under 35 U.S.C. 154(b) by 0 days.

(21) Appl. No.: 14/717,073

(22) Filed: May 20, 2015

(65) Prior Publication Data

US 2017/0105930 A1    Apr. 20, 2017

(51) Int. Cl.

| | | |
|---|---|---|
| *A61K 9/48* | (2006.01) | |
| *A61K 9/00* | (2006.01) | |
| *A61K 9/08* | (2006.01) | |
| *A61K 31/335* | (2006.01) | |
| *A61K 47/10* | (2017.01) | |
| *A61K 47/26* | (2006.01) | |
| *A61K 47/18* | (2017.01) | |
| *A61K 47/02* | (2006.01) | |

(52) U.S. Cl.
CPC .............. *A61K 9/0048* (2013.01); *A61K 9/08* (2013.01); *A61K 31/335* (2013.01); *A61K 47/02* (2013.01); *A61K 47/10* (2013.01); *A61K 47/186* (2013.01); *A61K 47/26* (2013.01)

(58) Field of Classification Search
None
See application file for complete search history.

(56) References Cited

U.S. PATENT DOCUMENTS

2012/0295967 A1* 11/2012 Gamache ............. A61K 9/0048
514/450

\* cited by examiner

*Primary Examiner* — Heidi Reese
(74) *Attorney, Agent, or Firm* — William D. Hare; McNeely, Hare & War LLP

(57) ABSTRACT

An aqueous ophthalmic solution containing a relatively high concentration of olopatadine in solubilized form is provided. The solution comprises a combination of at least two non-ionic surfactants and is essentially devoid of cyclodextrins. The solution is useful for providing enhanced relief from symptoms of ocular allergic disorders (e.g. conjunctivitis).

20 Claims, No Drawings

AQUEOUS OPHTHALMIC SOLUTION OF OLOPATADINE

BACKGROUND OF THE INVENTION (a) Field of the Invention

The present invention is directed to an aqueous ophthalmic solution of olopatadine or a pharmaceutically acceptable salt thereof. The solution contains a high concentration of olopatadine and a mixture of at least two non-ionic surfactants for providing enhanced solubility of olopatadine. The invention is further directed to the use of said solution for treating or providing enhanced relief from symptoms of ocular allergic disorders (e.g. conjunctivitis).

(b) Description of the Related Art

Olopatadine hydrochloride is a carboxylic acid derivative of doxepin, chemically described as 11-[(Z)-3(Dimethylamino) propylidene]-6-11dihydrodibenz [b,e] oxepin-2-acetic acid, hydrochloride [$C_{21}H_{23}NO_3 \cdot HCl$], as disclosed in U.S. Pat. Nos. 4,871,865 and 4,923,892 both assigned to Burroughs Wellcome. Olopatadine has antihistamine and antiasthmatic activity.

Olopatadine hydrochloride is commercially available in the United States as 0.1% and 0.2% sterile ophthalmic solutions under the brand names Patanol® and Pataday® respectively, both marketed by Alcon. According to its prescribing information, Patanol® is indicated for the treatment of signs and symptoms of allergic conjunctivitis and the approved ophthalmic solution contains olopatadine hydrochloride equivalent to 0.1% olopatadine, 0.01% benzalkonium chloride as preservative, dibasic sodium phosphate, sodium chloride, hydrochloric acid and/or sodium hydroxide (to adjust the pH) and purified water. The formulation has a pH of about 7, and osmolality of about 300 mOsm/kg. According to its prescribing information, Pataday® is indicated for the treatment of ocular itching associated with allergic conjunctivitis and the approved ophthalmic solution contains olopatadine hydrochloride equivalent to 0.2% olopatadine, 0.01% benzalkonium chloride as preservative, povidone, dibasic sodium phosphate, sodium chloride, edetate disodium, hydrochloric acid and/or sodium hydroxide (to adjust the pH) and purified water. The formulation has a pH of about 7, and osmolality of about 300 mOsm/kg.

A high concentration olopatadine product has been approved in the United Stated as 0.7% sterile ophthalmic solution under the brand name Pazeo®, marketed by Alcon. Pazeo® is indicated for the treatment of ocular itching associated with allergic conjunctivitis and the approved ophthalmic solution contains olopatadine hydrochloride equivalent to 0.7% olopatadine. Such a high concentration olopatadine formulation is believed to provide enhanced relief from symptoms of ocular allergic conjunctivitis, particularly late phase symptoms of ocular allergic conjunctivitis. The formulation contains povidone, hydroxypropyl-γ-cyclodextrin, polyethylene glycol 400, hydroxypropyl methylcellulose, boric acid, mannitol, benzalkonium chloride 0.015% (preservative), hydrochloric acid/sodium hydroxide (to adjust pH), and purified water.

Several formulations have been suggested in the art with an objective to prepare stable aqueous solution of olopatadine.

U.S. Pat. No. 6,995,186 discloses a topically administrable solution composition comprising approximately 0.17-0.62 w/v % olopatadine and a polymeric physical stability enhancing ingredient such as polyvinylpyrrolidone or polystyrene sulfonic acid.

U.S. Pat. No. 8,791,154 discloses an ophthalmic solution of olopatadine comprising at least 0.67 w/v % olopatadine and a cyclodextrin derivative along with other ingredients. The '154 patent teaches that the formulations containing a mixture of solubilizing agents such as polyethylene glycol, polyvinyl pyrrolidone, tyloxapol and other solubilizers do not provide long term stable composition of 0.7% w/v olopatadine and such composition begin to precipitate after some time.

PCT Application Pub. No. WO 2008093358 discloses an aqueous topical solution of olopatadine in concentrations ranging from about 0.17% to about 0.65% and further comprising a solubilizer selected from tyloxapol, vitamin E tocopheryl PEG diesters of dicarboxylic acids and mixtures thereof. The application further discloses that various solubilizers including hydroxypropyl-β-cyclodextrin (HP-β-CD), polysorbate 20, polysorbate 80, propylene glycol, hydroxypropyl methylcellulose 2910 (HPMC E4M premium), polyvinyl pyrrolidone K-30, xanthan gum, sodium carboxymethylcellulose (Sodium CMC), carbopol 934P, polyvinyl alcohol, and mixtures thereof are not sufficient to maintain olopatadine in solubilized form in the solution.

Indian Patent Application No: 748/MUM/2006 discloses a stable olopatadine hydrochloride solution containing hydroxypropyl-β-cyclodextrin as the stability enhancing ingredient so as to enhance the physical stability of the solution.

U.S. Patent Application Publication No. 20120022149 discloses ophthalmic compositions containing relatively high concentrations of a solubility enhancing polymer (e.g., polyether polymer such as PEG 4000 to 8000, polyvinyl polymer such as PVP or a combination thereof) for providing enhanced solubility of one or more therapeutic agents, preferably olopatadine.

U.S. Patent Application Publication No. 20110082145 discloses a combination formulation of olopatadine and a PDE4 inhibitor compound, and their use for treating and/or preventing allergic or inflammatory disorders of the eye, ear, skin, and nose. The concentration of olopatadine in the formulation may be at least 0.05% w/v and may contain polyethylene glycol and polyvinyl pyrrolidone as lubricants and/or viscosity agents, respectively.

The obstacle for preparing topical olopatadine aqueous solutions and particularly for high concentration olopatadine is the stability of the aqueous solutions over the shelf storage period. Olopatadine aqueous solutions of concentrations of 0.17% or higher were found to have physical stability problems during storage over the shelf life of the product. The olopatadine precipitates or crystallizes out of the formulated solution at concentrations higher than 0.17%. Solubilizing further high concentrations of olopatadine such as more than 0.67% w/v in a stable manner has proven even more difficult since olopatadine, by itself, is only soluble in water (pH about 7.0) at room temperature up to a concentration of about 0.18 w/v %.

Known solvents and polymers such as polyethylene glycol (PEG) 400 and polyvinyl pyrrolidone (PVP), when used at reasonably desirable concentrations, have proven incapable, alone or in combination, of solubilizing sufficient concentrations of olopatadine in compositions having approximately neutral pH. Further, it is also known that other solvents such as higher molecular weight PEGs such as PEG 6000 can significantly enhance solubility of olopatadine. However, such PEGs cause risk of discomfort when administered to humans.

Thus there is a need to create a desirable olopatadine formulation that not only solubilizes sufficient amounts of olopatadine, but also allows the formulation to achieve other desirable pharmaceutical characteristics. The present invention is directed at an ophthalmic composition that can provide high concentrations of olopatadine topically to the eye. Further, the present invention is directed to such a composition wherein the olopatadine is solubilized in solution in a stable manner.

SUMMARY OF THE INVENTION

The present invention provides an aqueous ophthalmic solution for treatment of allergic conjunctivitis. The solution comprises at least 0.67% w/v of olopatadine or a pharmaceutically acceptable salt thereof dissolved in the aqueous solution. The solution is typically devoid of cyclodextrin or any of its derivatives and contains a combination of at least two non-ionic surfactants.

In one aspect, the present invention provides an aqueous ophthalmic solution comprising:
(a) at least 0.67% w/v of olopatadine or a pharmaceutically acceptable salt thereof dissolved in a solution;
(b) at least two non-ionic surfactants; and
(c) water;
wherein said solution is devoid of cyclodextrin or a derivative thereof.

In a related aspect, the present invention provides an aqueous ophthalmic solution consisting essentially of or consisting of:
(a) at least 0.67% w/v of olopatadine or a pharmaceutically acceptable salt thereof dissolved in a solution;
(b) at least two non-ionic surfactants to solubilize the olopatadine; and
(c) water;
wherein said solution is devoid of cyclodextrin or a derivative thereof.

In another aspect, the present invention provides an aqueous ophthalmic solution comprising, consisting essentially of, or consisting of:
(a) at least 0.67% w/v of olopatadine or a pharmaceutically acceptable salt thereof dissolved in a solution;
(b) at least two non-ionic surfactants, wherein the non-ionic surfactants are tyloxapol and a polyoxyethylene sorbitan fatty acid ester; and
(c) water;
wherein said solution is devoid of cyclodextrin or a derivative thereof.

In another aspect, the present invention provides an aqueous ophthalmic solution comprising, consisting essentially of, or consisting of:
(a) at least 0.67% w/v of olopatadine or a pharmaceutically acceptable salt thereof dissolved in a solution;
(b) at least two non-ionic surfactants in concentration ranging from about 0.5 w/v but no greater than 10 w/v %, and preferably about 1 w/v % but no greater than 8 w/v %; and
(c) water;
wherein said solution is devoid of cyclodextrin or a derivative thereof.

In another aspect, the aqueous ophthalmic solution may comprise tyloxapol in a concentration ranging from about 0.01 w/v % but no greater than 5 w/v % and preferably about 0.1 w/v % but no greater than 3 w/v %.

In another aspect, the aqueous ophthalmic solution may comprise polyoxyethylene sorbitan fatty acid ester in concentration ranging from about 0.1 w/v % but no greater than 10 w/v % and preferably about 0.5 w/v % but no greater than 5 w/v %.

The polyoxyethylene sorbitan fatty acid ester may be selected from polyoxyethylene sorbitan monolaurate, polyoxyethylene sorbitan monopalmitate, polyoxyethylene sorbitan monostearate, polyoxyethylene soritan tristearate, polyoxyethylene sorbitan monooleate, polyoxyethylene sorbitan trioleate, polyoxyethylene sorbitan triisostearate, polyoxyethylene sorbitan monolaurate, polyoxyethylene sorbitol tetraoleate, or mixtures of two or more thereof. The preferred polyoxyethylene sorbitan fatty acid ester is polyoxyethylene sorbitan monooleate, and particularly its available grades such as polysorbate 20 or polysorbate 80.

In another aspect, the present invention provides an aqueous ophthalmic solution comprising, consisting essentially of, or consisting of:
(a) at least 0.67% w/v of olopatadine or a pharmaceutically acceptable salt thereof dissolved in a solution;
(b) at least two non-ionic surfactants, wherein the non-ionic surfactants are tyloxapol and polysorbate 80; and
(c) water;
wherein said solution is devoid of cyclodextrin or a derivative thereof.

In another aspect, the present invention provides an aqueous ophthalmic solution comprising, consisting essentially of, or consisting of:
(a) at least 0.67% w/v of olopatadine or a pharmaceutically acceptable salt thereof dissolved in a solution;
(b) at least two non-ionic surfactants;
(c) at least one preservative;
(d) at least one tonicity-adjusting agent; and
(e) water;
wherein said solution is devoid of cyclodextrin or a derivative thereof.

In another aspect, the present invention provides an aqueous ophthalmic solution comprising, consisting essentially of, or consisting of:
(a) at least 0.67% w/v of olopatadine or a pharmaceutically acceptable salt thereof dissolved in a solution;
(b) tyloxapol;
(c) polysorbate 80;
(d) benzalkonium chloride;
(e) sodium chloride; and
(f) water;
wherein said solution is devoid of cyclodextrin or a derivative thereof.

In another aspect, the present invention provides an aqueous ophthalmic solution comprising or consisting of:
(a) at least 0.67% w/v of olopatadine or a pharmaceutically acceptable salt thereof dissolved in a solution;
(b) 0.1 w/v % to 3 w/v % tyloxapol;
(c) 0.5 w/v % to 5 w/v % polysorbate 80;
(d) 0.001 w/v % to 0.05 w/v % benzalkonium chloride;
(e) 0.05 w/v % to 0.5 w/v % sodium chloride; and
(f) water;
wherein said solution is devoid of cyclodextrin or a derivative thereof.

In another aspect, the aqueous ophthalmic solution of the present invention optionally comprises at least one viscosity enhancing agent.

In another aspect, the aqueous ophthalmic solution present invention is devoid of cyclodextrin or a derivative thereof and solubility enhancing polymer.

In another aspect, the aqueous ophthalmic solution of the present invention is devoid of cyclodextrin or a derivative thereof and buffering agents.

In another aspect, the aqueous ophthalmic solution present invention is devoid of cyclodextrin or a derivative thereof, solubility enhancing polymer and buffering agents.

In another aspect, the present invention provides a method of treating at least one ocular allergy symptoms in humans, the method comprising topically applying to an eye of a human the solution as substantially described herein throughout the specification to treat at least ocular allergy symptom.

In another aspect, at least one ocular allergy symptom includes ocular itching.

The invention also contemplates a method of treating ocular allergy symptoms. The method will include topically applying a composition having a defined combination of the characteristics described above to an eye of a human. This step of topically applying the composition preferably includes dispensing an eye drop from an eyedropper.

Still other aspects and advantages of the invention will be apparent from the following detailed description of the invention.

DETAILED DESCRIPTION OF THE INVENTION

The present invention is predicated upon the provision of an aqueous ophthalmic composition in the form of a solution for the treatment of allergic conjunctivitis. The ophthalmic solution includes a relatively high concentration of olopatadine solubilized in an aqueous solution. The ophthalmic solution also includes a unique set of excipients for solubilizing the olopatadine while maintaining comfort of the solution and/or efficacy of the solution in treating symptoms associate with allergic conjunctivitis.

Many solubility issues can be addressed simply by providing one of many known surfactants or solubility enhancing agents to an ophthalmic composition to allow a sufficient concentration of therapeutic agent to be solubilized therein. However, the type of therapeutic agent, the desired concentration of therapeutic agents or other factors can give rise to solubility issues that cannot simply be addressed through the use of surfactants or they can require the use of undesirably high concentrations of surfactants. Finding solutions to such solubility issues can be extremely problematic.

For ophthalmic and other pharmaceutical compositions, the formulator of the composition not only needs to address the solubility issue, but will typically also need to address a host of other issues that can be brought about by attempts to increase therapeutic agent concentration. As one example, stability of a therapeutic agent can become more critical when a high concentration of therapeutic agent is employed. Larger amounts of unstable therapeutic agents will typically result in larger amounts of undesirable degradation products. As another example, the use of greater amounts of the solubility agent may cause incompatibility with the aqueous phase leading to an unstable product. Still further, and particularly for ophthalmic compositions, the use of greater amounts of solubility agent can cause an eye drop to be irritating to the eye.

The inventors of the present invention have surprisingly found that by using a combination of two non-ionic surfactants, an aqueous ophthalmic solution containing a high concentration of olopatadine in dissolved form can be prepared without employing cyclodextrin or its derivatives.

Unless indicated otherwise, all component amounts (i.e., concentrations) are presented on a weight volume percent (w/v %) basis and all references to concentrations of olopatadine are to olopatadine free base.

Olopatadine is a known compound that can be obtained by the methods disclosed in U.S. Pat. No. 5,116,863, the entire contents of which are hereby incorporated by reference in the present specification for all purposes. The formulation of the present invention contains at least 0.65%, more typically at least 0.67% or 0.68%, still more typically at least 0.7%, possibly at least 0.75% and even possibly at least 0.85% but typically no greater than 1.5% more typically no greater than 1.0%, still more typically no greater than 0.8%, possibly no greater than 0.75% and even possibly no greater than 0.72% of olopatadine where concentrations of olopatadine typically represent concentrations of olopatadine in free base form if the olopatadine is added to the solution as a salt. These lower limits of concentrations of olopatadine are particularly important since it has been found that efficacy of olopatadine in aqueous ophthalmic solutions in reducing late phase allergy symptoms and enhanced reduction of early phase redness begins to show improvement at concentrations greater than 0.5 w/v % of olopatadine and begins to show statistically significant improvements in reducing late phase allergy symptoms at concentrations of about 0.7 w/v % olopatadine and above (e.g., at least 0.65 w/v %, at least 0.67 w/v % or at least 0.68 w/v %). Most preferably, the concentration of the olopatadine in the solution is 0.7 w/v %.

Olopatadine may be added in the form of a pharmaceutically acceptable salt. Examples of the pharmaceutically acceptable salts of olopatadine include inorganic acid salts such as hydrochloride, hydrobromide, sulfate and phosphate; organic acid salts such as acetate, maleate, fumarate, tartrate and citrate; alkali metal salts such as sodium salt and potassium salt; alkaline earth metal salts such as magnesium salt and calcium salt; metal salts such as aluminum salt and zinc salt; and organic amine addition salts such as triethylamine addition salt (also known as tromethamine), morpholine addition salt and piperidine addition salt. The most preferred form of olopatadine for use in the solution compositions of the present invention is the hydrochloride salt of (Z)-11-β-dimethylaminopropylidene)-6,11-dihydro-dibenz[b,e]oxepin-2-acetic acid. When olopatadine is added to the compositions of the present invention in this salt form, 0.77% olopatadine hydrochloride is equivalent to 0.7% olopatadine free base, 0.88% olopatadine hydrochloride is equivalent to 0.8% olopatadine free base, and 0.99% olopatadine hydrochloride is equivalent to 0.9% olopatadine free base.

It is preferred that the entire concentration of olopatadine is dissolved in the solution as a water-based or aqueous solution. However, it is contemplated that olopatadine could be only partially dissolved. For example, a portion of the olopatadine could be in solution with the remainder being in suspension.

The aqueous ophthalmic solution of the invention comprises combination of at least two non-ionic surfactants. Suitable non-ionic surfactants include polymer of the alkyl aryl polyether alcohol like tyloxapol; polyoxyethylene polyoxypropylene polymer like triton X-100; polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, polyoxyethylene sorbitan trioleate, polyoxyethylene sorbitan triisostearate, polyoxyethylene sorbitan monolaurate, polyoxyethylene sorbitol tetraoleate; polyoxyethylene hydrogenated castor oils; sorbitan fatty acid esters such as sorbitan monooleate, sorbitan monolaurate, sorbitan monopalmitate and sorbitan monostearate; polyoxyethylene alkyl ethers such as polyoxyethylene lauryl ether; and polyoxyethylene fatty acid esters such as polyoxyethylene monostearate and mixtures thereof.

The aqueous ophthalmic solution of the present invention preferably includes a combination of tyloxapol and a polyoxyethylene sorbitan fatty acid ester to aid in solubilizing the olopatadine. The preferred polyoxyethylene sorbitan fatty acid ester is polyoxyethylene sorbitan monooleate, and particularly its available grades such as polysorbate 20 or polysorbate 80.

Tyloxapol is a non-ionic surfactant of the alkyl aryl polyether alcohol type, also known as superinone or triton. Chemically it is known as 4-(1,1,3,3-tetramethylbutyl) phenol polymer with formaldehyde and oxirane, and is commercially available from Rohm and Haas as Triton® X-200 and from Sigma Aldrich Chemicals.

The non-ionic surfactants are typically present in the composition at a concentration ranging from about 0.5 w/v % but no greater than 10 w/v %, and preferably about 1 w/v % but no greater than 8 w/v %.

The specific amount of non-ionic surfactants in a particular composition will typically depend upon the type or combination of types of non-ionic surfactants used. One particularly desirable non-ionic surfactant combination is tyloxapol and polysorbate 80.

Tyloxapol in the aqueous ophthalmic solution is used in concentrations ranging from about 0.01 w/v % to about 5 w/v % and more preferably used in concentrations ranging from about 0.1 w/v to about 3 w/v %.

Further, in U.S. Pat. No. 8,791,154, the entire contents of which are hereby incorporated by reference in the present specification for all purposes, it was known that a composition formed using a combination of solubilizing agents such as polyvinyl pyrrolidone, tyloxapol, polyethylene glycol and others to solubilize relatively high concentrations of olopatadine in the absence of polyoxyethylene sorbitan fatty acid ester will typically lack long term stability or shelf life. Such a composition typically begins to precipitate after undesirably short periods of time.

It was surprisingly found that the combination of at least two non-ionic surfactants is enough to solubilize 0.67 w/v % or more olopatadine. The inventors found that it is important to employ the polyoxyethylene sorbitan fatty acid ester in combination with tyloxapol.

In an embodiment, the aqueous ophthalmic solution present invention is devoid of cyclodextrin and solubility enhancing polymers such as polyethylene glycol, propylene glycol and lactam polymer (polyvinyl pyrrolidone).

In a further embodiment, the aqueous ophthalmic solution present invention is devoid of cyclodextrin and buffering agents such as lactic acid, citric acid, tartaric acid, phosphoric acid, acetic acid, hydrochloric acid, nitric acid, tromethamine, sodium or potassium metaphosphate, sodium or potassium phosphate, dibasic sodium phosphate dodecahydrate, sodium or potassium acetate, ammonia, sodium carbonate, sodium or potassium hydroxide, dibasic sodium phosphate and sodium borate.

In a preferred embodiment, the aqueous ophthalmic solution present invention is devoid of cyclodextrin, solubility enhancing polymers and buffering agents. By devoid of cyclodextrin, it should be understood that in one embodiment cyclodextrin may be present at insignificant quantities or in amounts with insignificant effect on the product.

It may also be desirable for the aqueous ophthalmic solution of the present invention to include a viscosity enhancing agent in order to enhance residence time of the solution upon the cornea when the composition is topically administered. Examples of potentially suitable viscosity enhancing agent include, without limitation, carboxyvinyl polymer, galactomannan, hyaluronic acid, cellulosic polymer, any combination thereof or the like. In a preferred embodiment, the ophthalmic composition includes hydroxyethyl cellulose (HEC), hydroxylpropylmethyl cellulose (HPMC) or both. One preferred HEC is sold under the tradename Nastrosol™ 250HX, which is commercially available from Hercules Incorporated, Aqualon Division, Argyle, Tex. One preferred HPMC is sold under the tradename E4M 2910 and is commercially available from Dow Chemical, Midland, Mich.

The amounts and molecular weights of HPMC and/or HEC used in the solution may depend upon the viscosity, osmolality and other attributes to be achieved for the solution. As used herein, viscosity is measured by a Brookfield viscometer (LVDVI+, CP-42, 12 RPM and a temperature of 25° C.). In a preferred embodiment, the viscosity of the solution is at least 2.0 centipoise (cps), more typically at least 15 cps, even more typically at least 21 cps and even possibly at least 27 cps, but is typically no greater than 65 cps, typically no greater than 40 cps, more typically no greater than 33 cps and even possibly no greater than 30 cps.

The preferred average molecular weight of HEC, when used, is typically in the range of 90,000 to 1,300,000 (e.g., approximately 1,000,000). The preferred average molecular weight of HPMC is typically in the range of 10,000 to 1,500,000 and more typically in the range of 189,000 to 688,000.

When HPMC is used alone, it is typically present in solution at a concentration that is at least 0.15% w/v, more typically at least 0.3% w/v and even more typically at least 0.5% w/v, but is typically no greater than 1.5% w/v, typically no greater than 1.0% w/v and is typically no greater than 0.7% w/v. When HEC is used alone, it is typically present in the solution at a concentration that is at least 0.1% w/v, more typically at least 0.25% w/v and even more typically at least 0.45% w/v, but is typically no greater than 1.4% w/v, typically no greater than 0.9% w/v and is typically no greater than 0.65% w/v.

Advantageously, when HPMC and HEC are used to together, they may produce a synergistic viscosity effect which allows the use of low concentrations of these excipients to produce the desired viscosity of the solution. When HPMC and HEC are used in combination, HPMC is typically present in solution at a concentration that is at least 0.05% w/v, more typically at least 0.1% w/v and even more typically at least 0.2% w/v, but is typically no greater than 1.0% w/v, typically no greater than 0.55% w/v and is typically no greater than 0.4% w/v. When HPMC and HEC are used in combination, HEC is typically present in solution at a concentration that is at least 0.02% w/v, more typically at least 0.06% w/v and even more typically at least 0.09% w/v, but is typically no greater than 0.6% w/v, typically no greater than 0.3% w/v and is typically no greater than 0.17% w/v.

The aqueous ophthalmic solution of the present invention may further include pharmaceutically acceptable excipients so as to provide a suitable carrier for the aqueous solution. The pharmaceutically acceptable carrier in the aqueous ophthalmic solution of the present invention may be selected from water (water for injection) or an aqueous system (that is an aqueous vehicle) comprising at least a major proportion of water. The carrier may include other liquid vehicles that are conventionally used in topical eye preparations.

The composition further can also include pharmaceutically acceptable excipients such as preservatives, tonicity-adjusting agents, chelating agents, pH adjusting agents, and antioxidants.

Suitable preservatives include, but are not limited to, hydrogen peroxide; sorbic acid; biquanides; quaternary ammonium salts such as benzalkonium chloride and benzethonium chloride; cationic compounds such as chlorhexidine gluconate; p-hydroxybenzoates such as methyl p-hydroxybenzoate, ethyl p-hydroxybenzoate, propyl p-hydroxybenzoate and butyl p-hydroxybenzoate; alcohol compounds such as chlorobutanol and benzyl alcohol; sodium dehydroacetate; thiomersal and the like. A particularly preferred preservative is a quaternary ammonium salt, such as benzalkonium chloride.

When used, the polymeric quaternary ammonium compound is generally used in the solution of the present invention in an amount that is greater than about 0.00001 w/v %, more typically greater than about 0.0003 w/v % and even more typically greater than about 0.0007 w/v % of the ophthalmic solution. Moreover, the polymeric quaternary ammonium compound is generally used in the solution of the present invention in an amount that is less than about 0.01 w/v %, more typically less than about 0.007 w/v %, even more typically less than 0.003 w/v %, still more typically less than 0.0022 w/v and even possibly less than about 0.0015 w/v % of the ophthalmic solution.

Benzalkonium chloride (BAK) is generally used in the solution of the present invention in an amount that is greater than about 0.001 w/v %, more typically greater than about 0.003 w/v % and even more typically greater than about 0.007 w/v % of the ophthalmic solution. Moreover, BAK is generally used in the solution of the present invention in an amount that is less than about 0.1 w/v %, and more typically less than about 0.03 w/v % of the ophthalmic composition.

Suitable tonicity-adjusting agents include, but are not limited to, mannitol, sodium chloride, glycerin, glucose, sorbitol and the like. Tonicity-adjusting agents may be present in concentrations ranging from about 0.01% w/v to about 1% w/v.

Suitable pH adjusting agents include, but are not limited to, hydrochloric acid, citric acid, phosphoric acid, acetic acid, tartaric acid, sodium hydroxide, potassium hydroxide, sodium carbonate, sodium hydrogen carbonate and the like.

Suitable chelating agents include, but are not limited to, edetate disodium, edetate trisodium, edetate tetrasodium, diethyleneamine pentaacetate and the like.

Suitable antioxidants include, but are not limited to, ascorbic acid, sodium ascorbate, tocopherol and sulfite salts like sodium sulfite, potassium sulfite, magnesium sulfite, calcium sulfite, sodium bisulfite, potassium bisulfite, magnesium bisulfite, calcium bisulfite, sodium metabisulfite, potassium metabisulfite, calcium metabisulfite, sodium thiosulfate, sodium hydrogen sulfite and the like.

The solution of the present invention will generally be formulated as sterile aqueous solutions. The solution of the present invention is also formulated so as to be compatible with the eye and/or other tissues to be treated with the solution. The ophthalmic solution intended for direct application to the eye will be formulated so as to have a pH and tonicity that are compatible with the eye.

The solution of the present invention will typically have a pH in the range of 4 to 9, preferably 5.5 to 8.5, and most preferably 5.5 to 8.0. Particularly desired pH ranges are 6.0 to 7.8 and more specifically 6.4 to 7.2. The solution will have an osmolality of 200 to 400 or 450 milliosmoles per kilogram (mOsm/kg), and more preferably 240 to 360 mOsm/kg.

It is generally preferred that the solution of the present invention be provided in an eye dropper that is configured to dispense the solution as eyedrops topically to the cornea of the eye. However, the desired size of a single eyedrop (i.e., droplet size) for the ophthalmic solution can be difficult to accomplish. It has been discovered that the cyclodextrin in the solution imparts a relatively high surface energy to the solution. In turn, droplet size tends to be relatively high. It has been discovered, however, that by dispensing droplets through a relatively small orifice and/or by maintaining the viscosity of the solution within the ranges discussed above, desired droplet size can be achieved. Desired droplet size is typically at least 10 µl, more typically at least 18 µl and even more typically at least 23 µl, but is typically no greater than 60 µl, typically no greater than 45 µl and is typically no greater than 33 µl. Advantageously, this droplet size for the solution with the concentrations of olopatadine specified herein allows an individual to dispense one droplet per eye once a day and receive relief from symptoms of ocular allergic conjunctivitis generally, but particularly receive relief from late phase symptoms of ocular allergic conjunctivitis.

In a preferred embodiment, the solution of the present invention is a multi-dose solution that has sufficient antimicrobial activity to allow the solution to satisfy the USP preservative efficacy requirements, as well as other preservative efficacy standards for aqueous pharmaceutical solutions.

The aqueous solution of the present invention is physically and chemically stable. The term "'chemically stable" as used herein means that the aqueous solution when stored on the shelf for up to two years has less than 2% total degradation products as determined by the area normalization method. The chemical stability may be assessed by accelerated stability testing. The aqueous solution of the present invention may be stored in a closed container at 30° C./65% relative humidity or 40° C./75% relative humidity or 2-8° C. (refrigeration condition) and andyzed at one month duration for up to three months or six months. It is generally accepted that a product is stable on the shelf over a period of two years if the product is stable for three months at an accelerated stability test condition of 40° C./75% relative humidity.

The term "physically stable" as used herein means that when an aqueous solution of the present invention is stored in a closed container crystals of olopatadine do not appear.

Example 1: Olopatadine Hydrochloride 0.7 w/v % Ophthalmic Solution

TABLE 1

| Sr. No. | Ingredients | Composition A (% w/v) | Composition B (% w/v) | Composition C (% w/v) |
|---|---|---|---|---|
| 1 | Olopatadine Hydrochloride | 0.0776* | 0.0776* | 0.0776* |
| 2 | Tyloxapol | 0.3 | 1.0 | 1.5 |
| 3 | Polysorbate 80 | 2.0 | 3.0 | 4.0 |
| 4 | Benzalkonium Chloride | 0.01 | 0.0125 | 0.015 |
| 5 | Sodium Chloride | 0.15 | 0.20 | 0.25 |
| 6 | Hydrochloric Acid/ Sodium Hydroxide | QS to adjust pH | QS to adjust pH | QS to adjust pH |
| 7 | Purified Water | QS | QS | QS |

*equivalent to 0.7% Olopatadine Base

Procedure:

Tyloxapol was added and mixed in a sufficient quantity of purified water until fully dissolved. Polysorbate 80 was added to the solution and mixed until fully dissolved.

Olopatadine hydrochloride, sodium chloride and benzalkonium chloride were sequentially added to the solution and mixed until dissolved. Hydrochloric acid or sodium hydroxide was then added to the resulting solution to adjust the pH in the range of 6.0 to 7.5.

What is claimed is:

1. An aqueous ophthalmic solution comprising:
   (a) at least 0.67% w/v of olopatadine or a pharmaceutically acceptable salt thereof dissolved in a solution;
   (b) at least two non-ionic surfactants; and
   (c) water;
   wherein said solution is devoid of cyclodextrin or a derivative thereof.

2. The aqueous ophthalmic solution of claim 1, wherein olopatadine or a pharmaceutically acceptable salt thereof is dissolved in the solution in a concentration of about 0.7 w/v %.

3. The aqueous ophthalmic solution of claim 1, wherein the non-ionic surfactants are tyloxapol and a polyoxyethylene sorbitan fatty acid ester.

4. The aqueous ophthalmic solution of claim 1, wherein a concentration of the non-ionic surfactants ranges from about 0.5 w/v % to no greater than 10 w/v %.

5. The aqueous ophthalmic solution of claim 3, wherein a concentration of tyloxapol ranges from about 0.01 w/v % to no greater than 5 w/v %.

6. The aqueous ophthalmic solution of claim 3, wherein said polyoxyethylene sorbitan fatty acid ester is selected from the group consisting of polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, polyoxyethylene sorbitan trioleate, polyoxyethylene sorbitan triisostearate, polyoxyethylene sorbitan monolaurate, and polyoxyethylene sorbitol tetraoleate.

7. The aqueous ophthalmic solution of claim 6, wherein said polyoxyethylene sorbitan fatty acid ester is polyoxyethylene sorbitan monooleate.

8. The aqueous ophthalmic solution of claim 5, wherein said polyoxyethylene sorbitan monooleate is selected from polysorbate 20, polysorbate 80 or their mixtures.

9. The aqueous ophthalmic solution of claim 3, wherein a concentration of said polyoxyethylene sorbitan fatty acid ester ranges from about 0.1 w/v % to no greater than 10 w/v %.

10. The aqueous ophthalmic solution of claim 1, wherein said solution is devoid of solubility enhancing polymers.

11. The aqueous ophthalmic solution of claim 1, wherein said solution is devoid of buffering agents.

12. The aqueous ophthalmic solution of claim 1, further comprising at least one viscosity enhancing agent.

13. The aqueous ophthalmic solution of claim 1, consisting essentially of:
   (a) at least 0.67% w/v of olopatadine or a pharmaceutically acceptable salt thereof dissolved in a solution;
   (b) at least two non-ionic surfactants for solubilizing the olopatadine; and
   (c) water;
   wherein said solution is devoid of cyclodextrin or a derivative thereof.

14. An aqueous ophthalmic solution comprising:
   (a) at least 0.67% w/v of olopatadine or a pharmaceutically acceptable salt thereof dissolved in a solution;
   (b) at least two non-ionic surfactants;
   (c) at least one preservative;
   (d) at least one tonicity-adjusting agent; and
   (e) water;
   wherein said solution is devoid of cyclodextrin or a derivative thereof.

15. The aqueous ophthalmic solution of claim 14, consisting of:
   (a) at least 0.67% w/v of olopatadine or a pharmaceutically acceptable salt thereof dissolved in a solution;
   (b) at least two non-ionic surfactants;
   (c) at least one preservative;
   (d) at least one tonicity-adjusting agent; and
   (e) water;
   wherein said solution is devoid of cyclodextrin or a derivative thereof.

16. The aqueous ophthalmic solution of claim 14, consisting of:
   (a) at least 0.67% w/v of olopatadine or a pharmaceutically acceptable salt thereof dissolved in a solution;
   (b) two non-ionic surfactants;
   (c) a preservative;
   (d) a tonicity-adjusting agent; and
   (e) water;
   wherein said solution is devoid of cyclodextrin or a derivative thereof.

17. An aqueous ophthalmic solution comprising:
   (a) at least 0.67% w/v of olopatadine or a pharmaceutically acceptable salt thereof dissolved in a solution;
   (b) tyloxapol;
   (c) polysorbate 80;
   (d) benzalkonium chloride;
   (e) sodium chloride; and
   (f) water;
   wherein said composition is devoid of cyclodextrin or a derivative thereof.

18. The aqueous ophthalmic solution of claim 17, consisting of:
   (a) at least 0.67% w/v of olopatadine or a pharmaceutically acceptable salt thereof dissolved in a solution;
   (b) tyloxapol;
   (c) polysorbate 80;
   (d) benzalkonium chloride;
   (e) sodium chloride; and
   (f) water;
   wherein said composition is devoid of cyclodextrin or a derivative thereof.

19. A method of treating at least one ocular allergy symptoms in humans, the method comprising topically applying to an eye of a human the aqueous ophthalmic solution of claim 1 to treat at least ocular allergy symptom.

20. The method of claim 19, wherein the at least one ocular allergy symptom includes ocular itching.

* * * * *